US005571042A

United States Patent [19]
Abbate et al.

[11] Patent Number: 5,571,042
[45] Date of Patent: Nov. 5, 1996

[54] APPARATUS FOR PRODUCING HOLLOW GROUND NEEDLES

[75] Inventors: Richard Abbate, Killingworth; Said Rizk, Monroe; Michael Haroldsen, Botsford; Timothy D. Kosa, Milford, all of Conn.

[73] Assignee: United States Surgical Corporation, Norwalk, Conn.

[21] Appl. No.: 104,304

[22] Filed: Aug. 9, 1993

Related U.S. Application Data

[63] Continuation-in-part of Ser. No. 959,326, Oct. 9, 1992, Pat. No. 5,388,373.

[51] Int. Cl.$^6$ ................................................. B24B 19/16
[52] U.S. Cl. .............................................. 451/59; 451/57
[58] Field of Search .......................... 451/65, 59, 296, 451/306, 311, 310, 382, 57

[56] References Cited

U.S. PATENT DOCUMENTS

| | | |
|---|---|---|
| 160,686 | 3/1875 | Kingman . |
| 279,075 | 6/1883 | Berry ........................................ 451/58 |
| 2,215,752 | 9/1940 | Enya . |
| 2,353,683 | 7/1944 | Martines . |
| 2,452,205 | 10/1945 | Newton . |
| 2,838,883 | 6/1958 | Hall . |
| 3,539,314 | 11/1970 | Rockefeller et al. . |
| 4,063,906 | 12/1977 | Wetzels . |
| 4,112,625 | 9/1978 | Wetzels . |
| 4,173,100 | 11/1979 | MacBroom, Jr. . |
| 4,216,628 | 8/1980 | Wada . |
| 4,441,280 | 4/1984 | Wetzels et al. . |
| 5,155,943 | 10/1992 | Matsutani et al. . |

FOREIGN PATENT DOCUMENTS

| | | |
|---|---|---|
| 0282440 | 9/1988 | European Pat. Off. . |
| 4304684A1 | 9/1993 | Germany . |
| 4304684 | 9/1993 | Germany . |
| 1048934 | 4/1962 | United Kingdom . |
| 2006063 | 5/1979 | United Kingdom . |

OTHER PUBLICATIONS

Patent Abstracts of Japan Publication No. JP-A-60048249 dated Mar. 15, 1985.
Industrial Diamond Review, Aug. 1971, London GB, pp. 314–316, Chaika, "Manufacturing Complex-profile Carbide tools and parts with diamond form grinding wheels".
Copy of Search Report from Corresponding European Patent application No. 94111489.4.

*Primary Examiner*—Robert A. Rose

[57] ABSTRACT

An apparatus for applying a cutting edge on surgical needles having at least one abrading device and a needle holding mechanism. The abrading device includes an abrasive member such as a rotatable abrasive belt or grinding wheel. The needle holding mechanism is positionable for selectively engaging an end of at least one needle with the abrading device to provide a cutting edge on the needle. A grinding wheel may be provided for hollow grinding the surgical needles, the grinding wheel including a cylindrical member having a plurality of ridges. The cylindrical member preferably has a super-abrasive coating of diamond or boron nitride particles electroplated thereon.

21 Claims, 13 Drawing Sheets

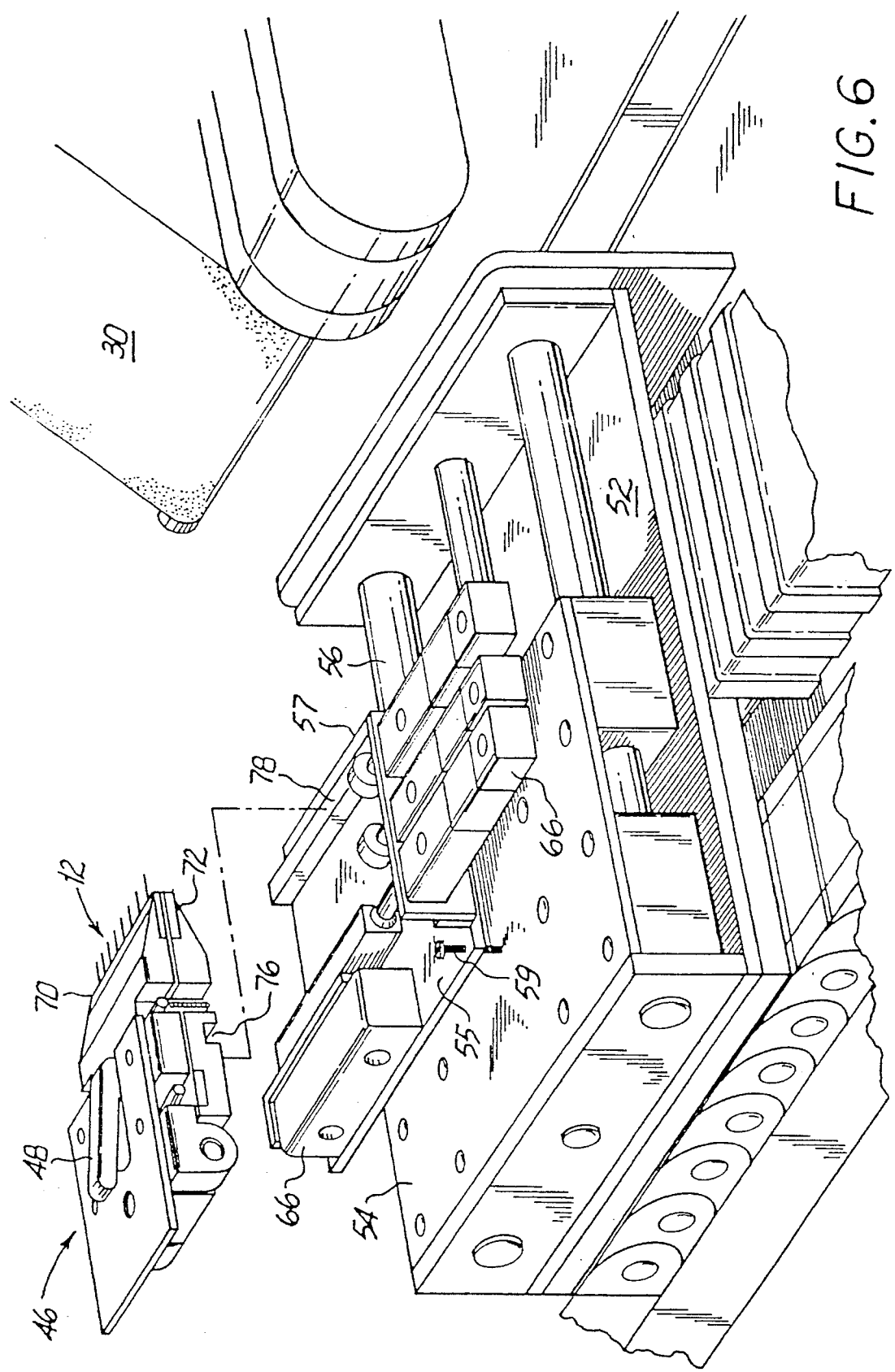

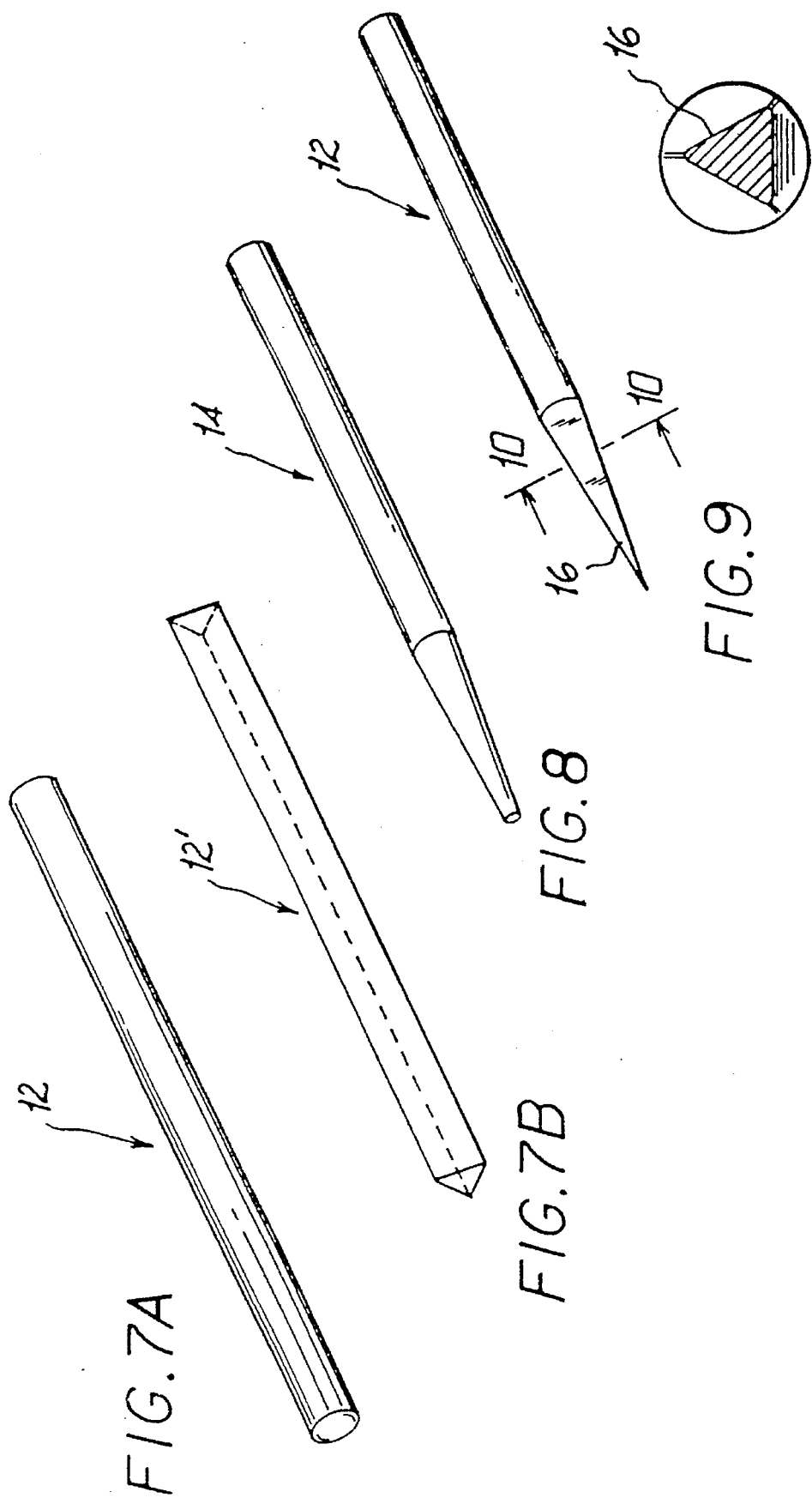

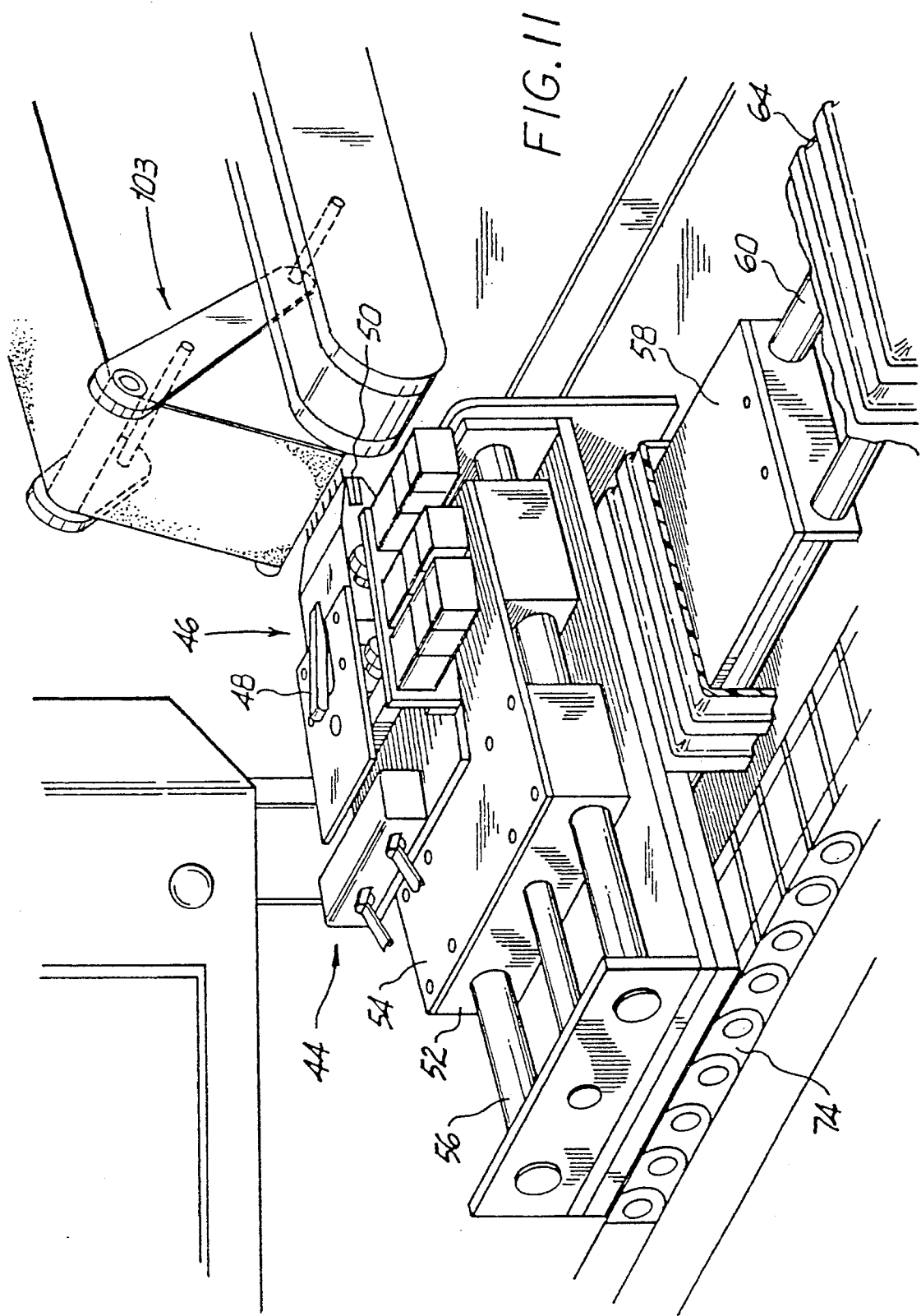

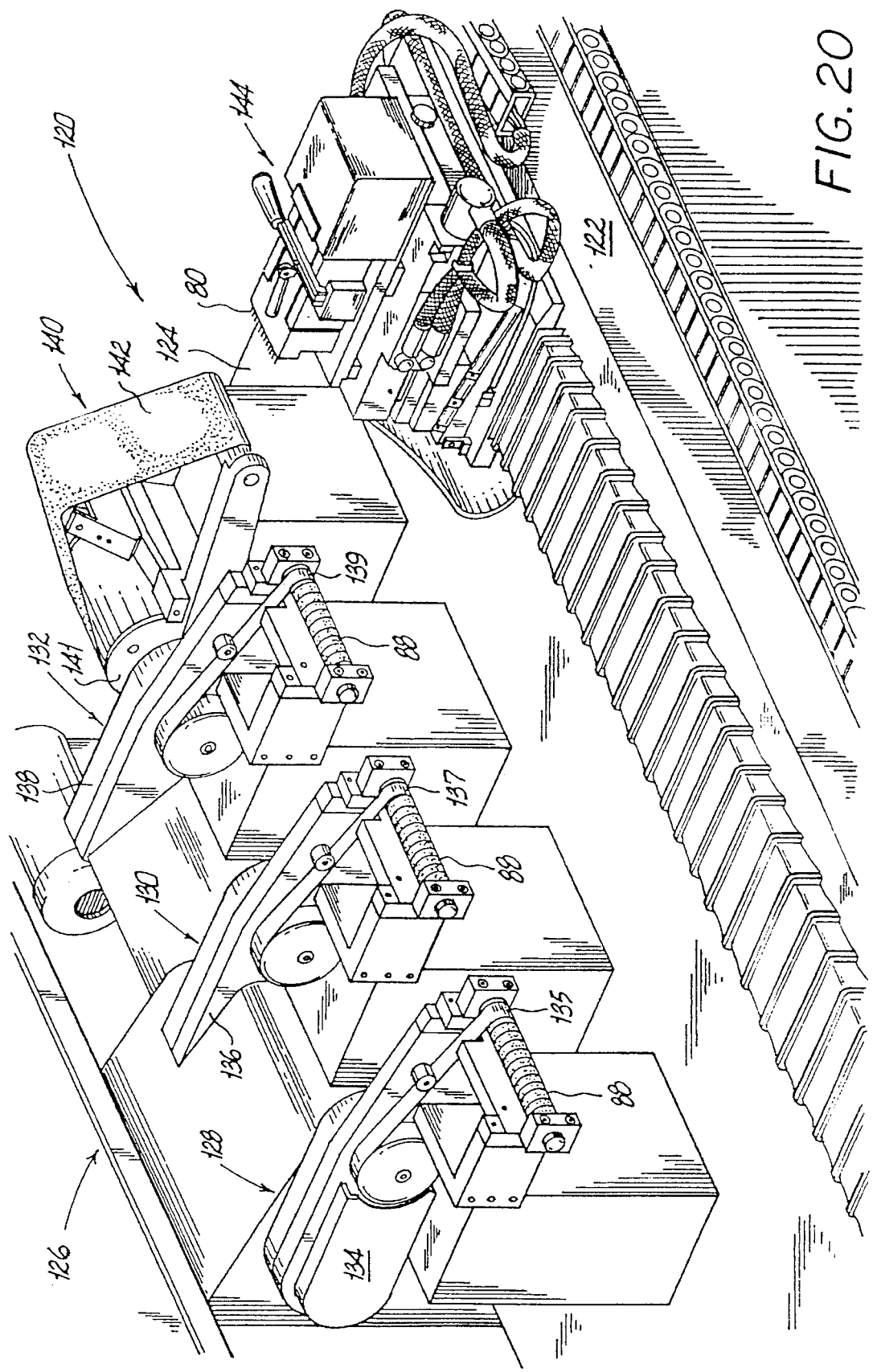

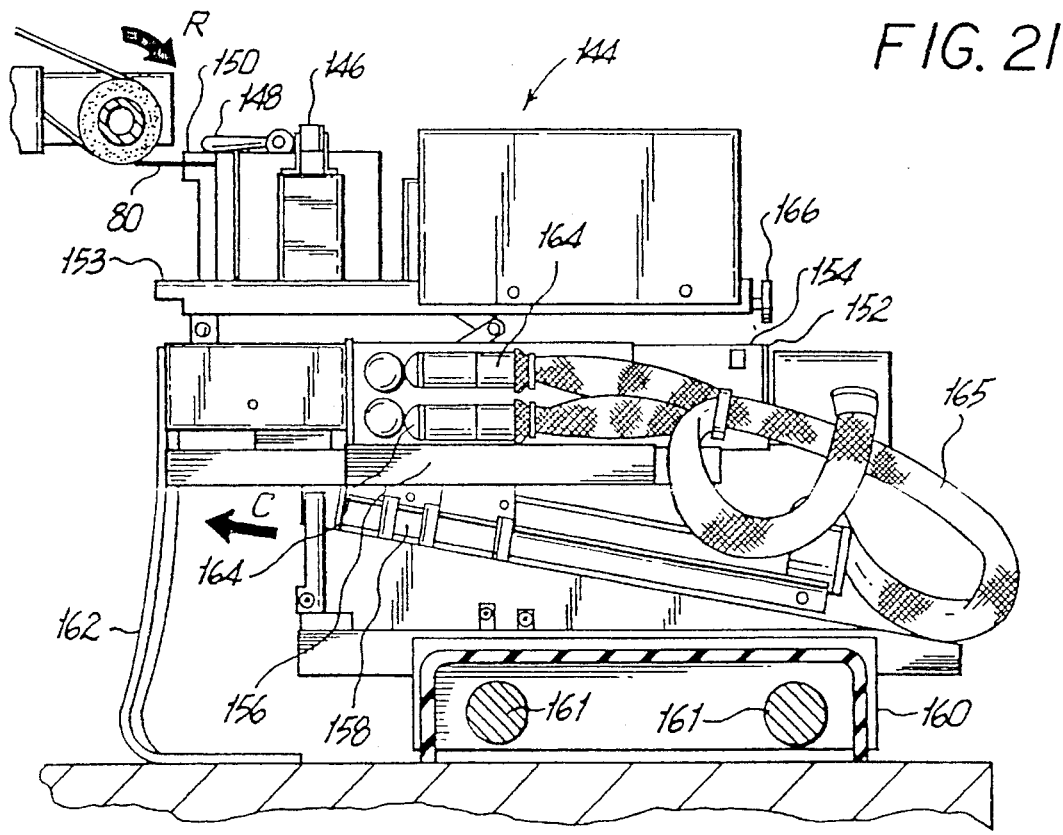
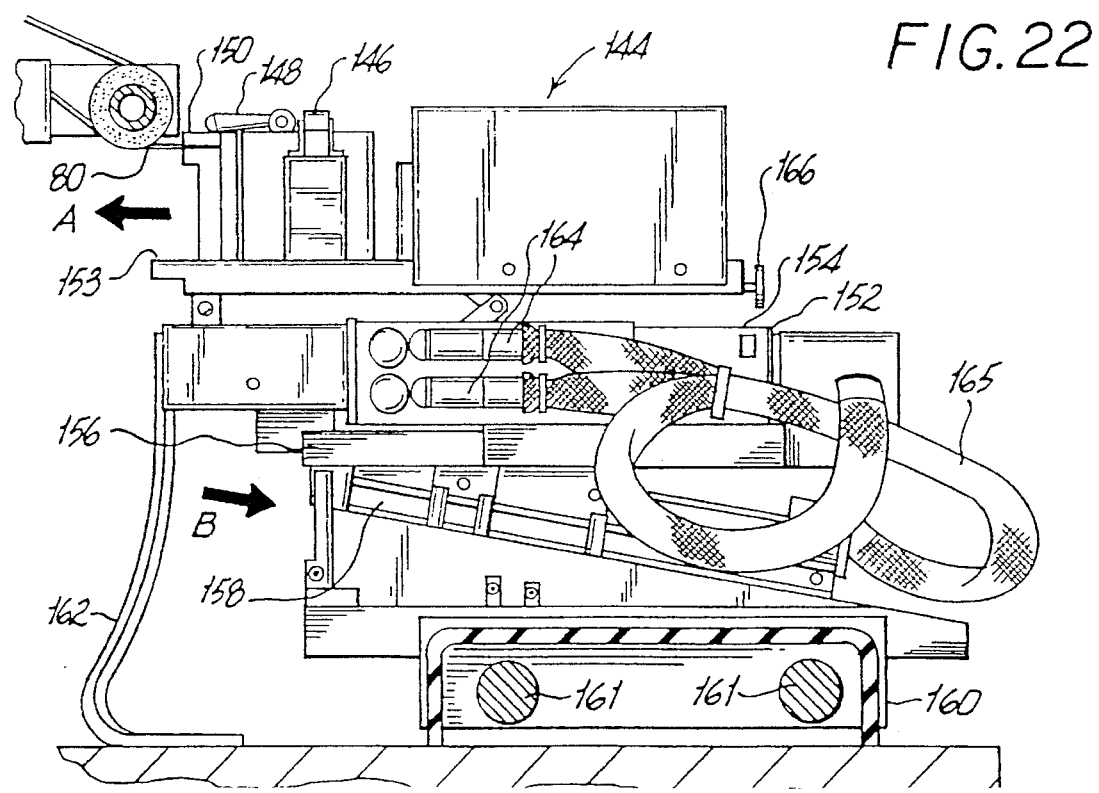

APPARATUS FOR PRODUCING HOLLOW GROUND NEEDLES

CROSS REFERENCE TO RELATED APPLICATION

This application is a continuation-in-part of prior application Ser. No. 07/959,326, filed Oct. 9, 1992 now U.S. Pat. No. 5,388,373.

BACKGROUND OF THE INVENTION

1. Field of the Invention

The present invention relates to devices for grinding surgical needles, and more particularly to devices, including grinding wheels, for abrading the needle to provide a surgical cutting edge on the needle through the use of an abrasive surface for grinding and/or polishing a needle, or a multiplicity of needles, simultaneously. The present invention additionally relates to an apparatus and a grinding wheel for producing hollow ground surgical needles.

2. Description of the Related Art

Surgical needle manufacture is a precise and time consuming procedure, particularly where individual needles are formed one at a time. Conventional surgical needle manufacturing typically begins with the step of cutting round wire stock to a predetermined length to form a needle blank. One end of the blank is then tapered to provide a point thereon. In some instances, such as for example in plastic surgery needles or taper cutting edge needles, a cutting edge must be formed at or near the point of the needle. To provide a cutting edge, the tapered end of the needle is stamped or pressed and then subjected to grinding and/or polishing to sharpen its longitudinal edges. Normally, at least a portion of the needle blank is pressed to provide flat surfaces on a portion of the needle to facilitate grinding. After the cutting edge is formed on the needle, the needle blank is cut to its final desired length and then prepared for suture attachment. The needle may be further subjected to additional steps such as polishing or hardening.

Conventional needle processing is in large part a manual operation. Providing a cutting edge, for example, typically includes the steps of: grasping and holding a needle using a hand held device; manually moving the needle into contact with a rotating abrasive belt or grinding wheel; visually evaluating and/or confirming the progress of needle cutting edge formation; and repeating the steps of manually contacting the needle with the abrasive surface and visually checking the progress of the cutting edge formation for each edge to be applied to the needle. Since visual confirmation of a specified cutting edge in the view of the person performing the operation is required, the reproducibility, accuracy and hence quality of the cutting edge is largely a function of the skill and experience of the operator.

More specifically, in the prior art the needle may be held by a pliers-like device or a chuck which grips an end of the needle opposite from the end of the needle where the cutting edge is to be applied. Usually, no more than two needles can be held in the device at one time, and the pliers-like device or chuck is used to manually engage the needle end with a rotating abrasive belt or wheel. The end of the needle is maintained in contact with the abrasive belt or wheel until the desired cutting edge is fashioned.

Grinding wheels used in previously known methods are typically of the bonded type and generally require frequent redressing. During use, the abrasive grains on bonded grinding wheels become slightly dulled. Normal stresses in the grinding operation tear the worn grain from the wheel to expose a new cutting grain. A soft wheel wears too fast, losing grains before they are dulled, whereas too hard a wheel develops a smooth glazed surface which does not cut properly. As the abrasive wears, the configuration of the wheel surface changes enough to affect the grind on the finished product. When this occurs the wheel must then be re-dressed to open new abrasive grain surfaces or to recondition the grinding surface. The re-dressing is performed manually and may vary from operator to operator. Even slight variances may cause needle geometries to depart from the strict specifications, thereby resulting in a higher percentage of rejected parts and concomitant higher costs.

Needle sharpness, both of its point and cutting edges, is an important factor during many surgical procedures. The surgeon's ability to perform delicate suturing operations is severely limited by needles with points and edges which are not sharp or which do not remain sharp. While flat pressing facilitates the formation of a needle edge, there is yet need of a way to increase and maintain the sharpness to which the cutting edge of a needle can be ground.

One disadvantage to conventional needle abrading devices is that manually positioning needles for abrading can be irregular and inefficient. Additionally, the engagement and extent of the needle processing is visually monitored which can result in an inconsistent needle cutting edge. Another disadvantage of the conventional methods is the reliance on visual affirmation of the needle cutting edge which can be ineffective for meeting precise surgical needle specifications. Finally, the prior art devices provide for substantially little or no automation so that the process is time consuming.

The novel device for applying a cutting edge to a surgical needle obviates the disadvantages encountered in the prior art and provides a device for automatically processing a plurality of needles at the same time. The device provides consistent and reproducible results, particularly with respect to needle geometry and surface finish, which ensures precision and accuracy in the application of cutting edges to needles during large scale manufacture. The device provides for both grinding the cutting edges onto the needle, as well as polishing and deburring to produce the finished product. The device also permits the application of cutting edges on several sides of the surgical needle without necessitating the removal and repositioning of the needles in the device to result in a precision multi-sided cutting edge surgical needle.

SUMMARY OF THE INVENTION

An apparatus for applying a cutting edge to surgical needles is provided which includes a frame for mounting at least one device for abrading the needles and a needle holding mechanism for securing the needles and moving the needles into engagement with the abrading device. The abrading device and the needle holding mechanism are positioned on the frame such that needles can be processed in an automated and efficient manner. The needle holding mechanism may hold a plurality of needle blanks to simultaneously engage the blanks with the abrading devices to provide a substantially identical cutting edge on each of the blanks. It is further contemplated that the needle holding mechanism is capable of rotating the needles to consecutively engage various sides of the needle to provide a multi-sided cutting edge.

The abrading device preferably comprises a motor driven rotatable abrasive member, which rotates the abrasive member at a predetermined speed. The needle holding mechanism is movably mounted to the frame and is selectively positionable in relation to the abrading device. Preferably, the apparatus may provide a plurality of needle abrading devices positioned on the frame, each including at least one rotatable abrasive belt or wheel.

The needle holding mechanism selectively engages the needles with the abrasive belts at each of the needle abrading devices. The holding mechanism moves the needles into and out of engagement with the abrasive belts or wheels of the abrading devices. The needle holding mechanism transports the needles to a position substantially perpendicular to each abrading device.

The needles are engagable with the abrasive belt or wheel of each of the abrading devices at predeterminable selectable time intervals. The motion of the needle holding mechanism is hydraulically activated in conjunction with a programmable logic controller which automates the entire process. Hydraulic cylinders move the needles in the needle holding mechanism toward and away from the belt or wheel at each abrading device to engage an end of each needle with the belt or wheel. Hydraulic cylinders also move the needle holding mechanism to move the needles along an axis parallel to the abrading devices so that the needles can be positioned adjacent to each abrasive belt or wheel to be engaged with that belt.

In a second embodiment an angled plate and track are provided in the needle holding mechanism to enable the mechanism to provide a compound motion to the needles as they engage the abrading devices. Preferably, the plate is oriented at an angle relative to the longitudinal axis of the needles. Hydraulic cylinders also move the needle holding mechanism along the angled plate to provide an up and down movement which can be synchronized with the inward and outward movement to provide a multi-axis compound movement of the needle holding mechanism relative to the abrading devices.

Additionally, a method and apparatus are provided herein for "hollow grinding" needle blanks. The apparatus includes a generally cylindrical grinding wheel having a plurality of precisely spaced apart circumferential grinding ridges. The abrasive surface of the grinding wheels preferably comprises an electroplated superabrasive material such as diamond or boron nitride. In a method for hollowing grinding, elongated needle blanks, preferably having a triangular cross section and three flat sides, are placed in a holder and contacted against the rotating grinding wheel to produce a concave depression oriented along the length of the needle blank. A needle blank can thus be formed with three hollowed sides. The needle blanks may be tapered by grinding to a sharp point and may subsequently be polished and bent into a curved configuration.

BRIEF DESCRIPTION OF THE DRAWINGS

The foregoing features of the present invention will become more readily apparent and will be understood by referring to the following detailed description of preferred embodiments of the invention, which are described hereinbelow with reference to the drawings wherein:

FIG. 6 is an enlarged perspective view of the apparatus of FIG. 2 with the needle holding mechanism in an exploded view;

FIGS. 7A, 7B and 8 are perspective views illustrating stock needles prior to the application of a cutting edge;

FIG. 9 is a perspective view illustrating a needle having a cutting edge applied thereon;

FIG. 10 is a cross-sectional view of the cutting edge of the needle shown in FIG. 9 taken along lines 10—10;

FIG. 11 is a perspective view illustrating an alternate embodiment of the apparatus of the present invention;

FIG. 20 is a perspective view of another embodiment of a grinding apparatus according to the present invention;

FIG. 21 is an enlarged perspective view illustrating the 4-axis needle transport mechanism; and FIG. 22 is a view similar to that of FIG. 21 during a grinding sequence.

DETAILED DESCRIPTION OF PREFERRED EMBODIMENTS

Figure 1:
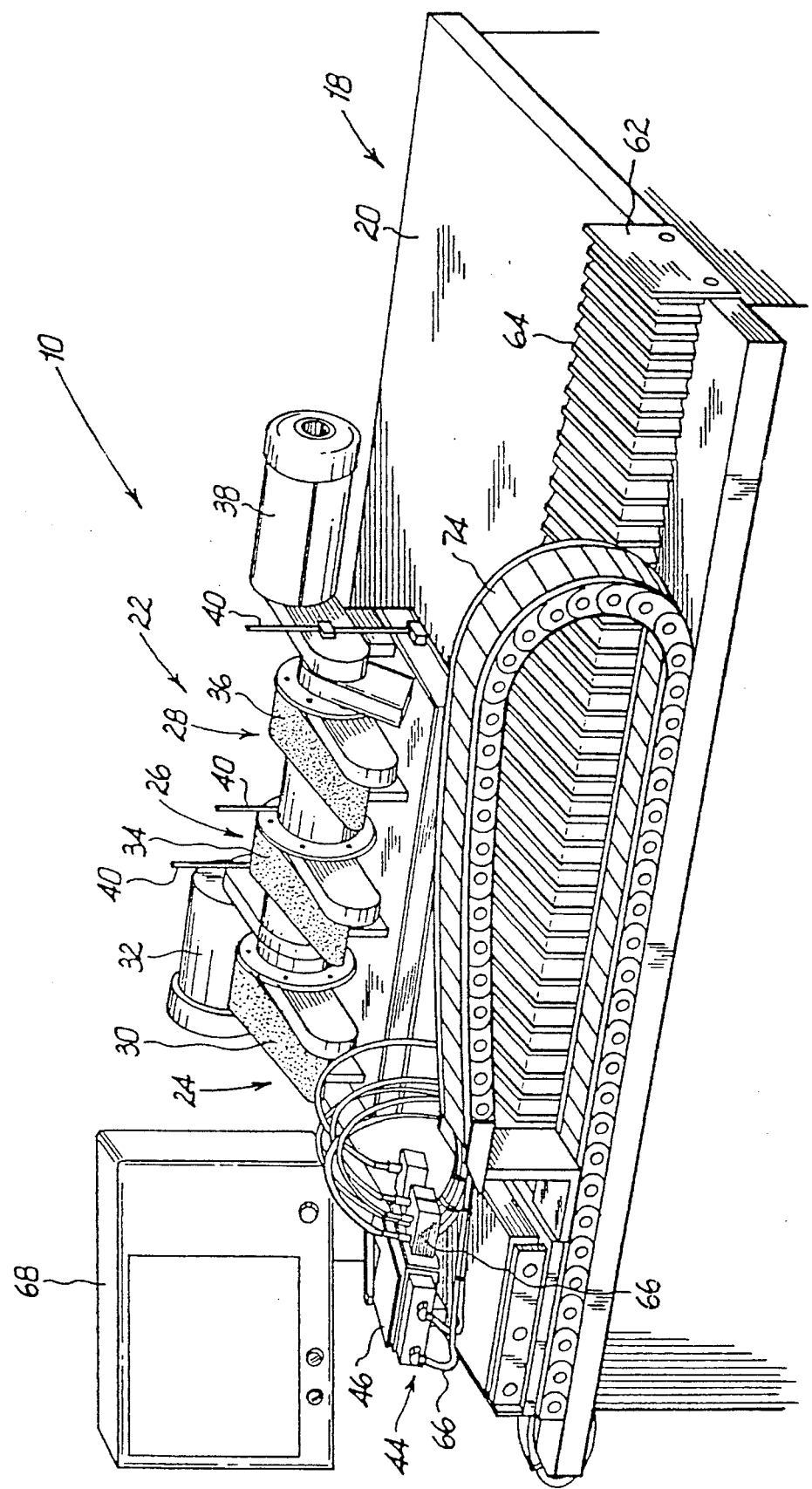
FIG. 1 is a perspective view illustrating an apparatus for applying a cutting edge to a needle according to the present invention.

Referring to the drawings, in which like reference numerals identify identical or similar elements, there is illustrated a preferred embodiment of an apparatus 10 for applying a cutting edge to surgical needles. Apparatus 10 processes stock needle blanks, such as blank 12, 12' shown in FIGS. 7A and 7B, respectively, or a pre-tapered blank 14 as shown in FIG. 8. A portion of the needle blank may be coined or flat pressed to impart a desired cross-sectional shape to the needle blank prior to processing by apparatus 10. Apparatus 10 applies at least one cutting edge 16 on blank 12, and in a preferred embodiment, three edges 16 are applied as seen in FIGS. 9 and 10.

Referring to Figs. I and 2, the apparatus 10 includes a frame or table 18 having a working surface 20. The apparatus 10 comprises a series of abrading stations 22 positioned on the work surface 20 for abrading a multiplicity of needles to apply cutting edges thereon. The abrading stations 22 refine the needle blank 12 in sequential stages using rotating abrasive devices such as grinding belts or grinding stones and wheels. Each abrading device of the station 22 preferably represents a predetermined stage of needle refinement.

The present invention processes a needle blank 12 to result in three cutting edges 16 utilizing three separate abrading devices 24, 26 and 28. Alternative embodiments, however, may have more or less than three abrading devices, and further may provide cutting edges on more or less than three sides.

As best seen in FIGS. 1 and 3–5, the first abrading device 24 includes a first rotatable abrasive belt 30 rotated at a desirable speed by a motor 32. The first abrasive belt 30 fashions a cutting edge on a needle by grinding an end of the needle blank 12. The first belt 30 has an abrasiveness for grinding an initial cutting edge on the end of a needle blank 12.

A second abrading device 26 is positioned laterally adjacent and along a common axis with the first abrading device 24. The second abrading device 26 includes a second rotatable abrasive belt 34 for further abrading blank 12 to apply the cutting edge on the needle blank 12.

The second belt 34 can also be rotated by motor 28. Preferably, however, another motor is used to rotate second belt 34 to allow a different grinding speed in connection with second belt 34. Different grinding speeds may be desirable for belts containing different abrasives, depending on factors such as abrasive composition or grit size. The second abrasive belt 34, preferably, is less abrasive than the first belt 30 to further refine the cutting edge after engagement with the first abrasive belt 30. In another embodiment, it is also contemplated that the second abrasive belt 34 could be equally or more abrasive than the first belt.

A third abrading device 28 is positioned laterally adjacent to and along a common axis with the first two abrading devices 24 and 26. The third abrading device 28 includes a third rotatable abrasive belt 36 rotated by motor 38 at a predetermined speed. Preferably, the abrasiveness of the third belt 36 is less than the abrasiveness of the second abrasive belt 34, and is particularly adapted for polishing the needle cutting edge 16 to deburr the edge applied by the first two abrading devices 24 and 26. The third belt 36 may comprise a velvet flock belt to provide for deburring and polishing. However, deburring may also be accomplished by reversing the direction of third belt 36. Also, the speed of the motor 38 may be adjusted for optimum polishing of the cutting edge.

Figure 3:
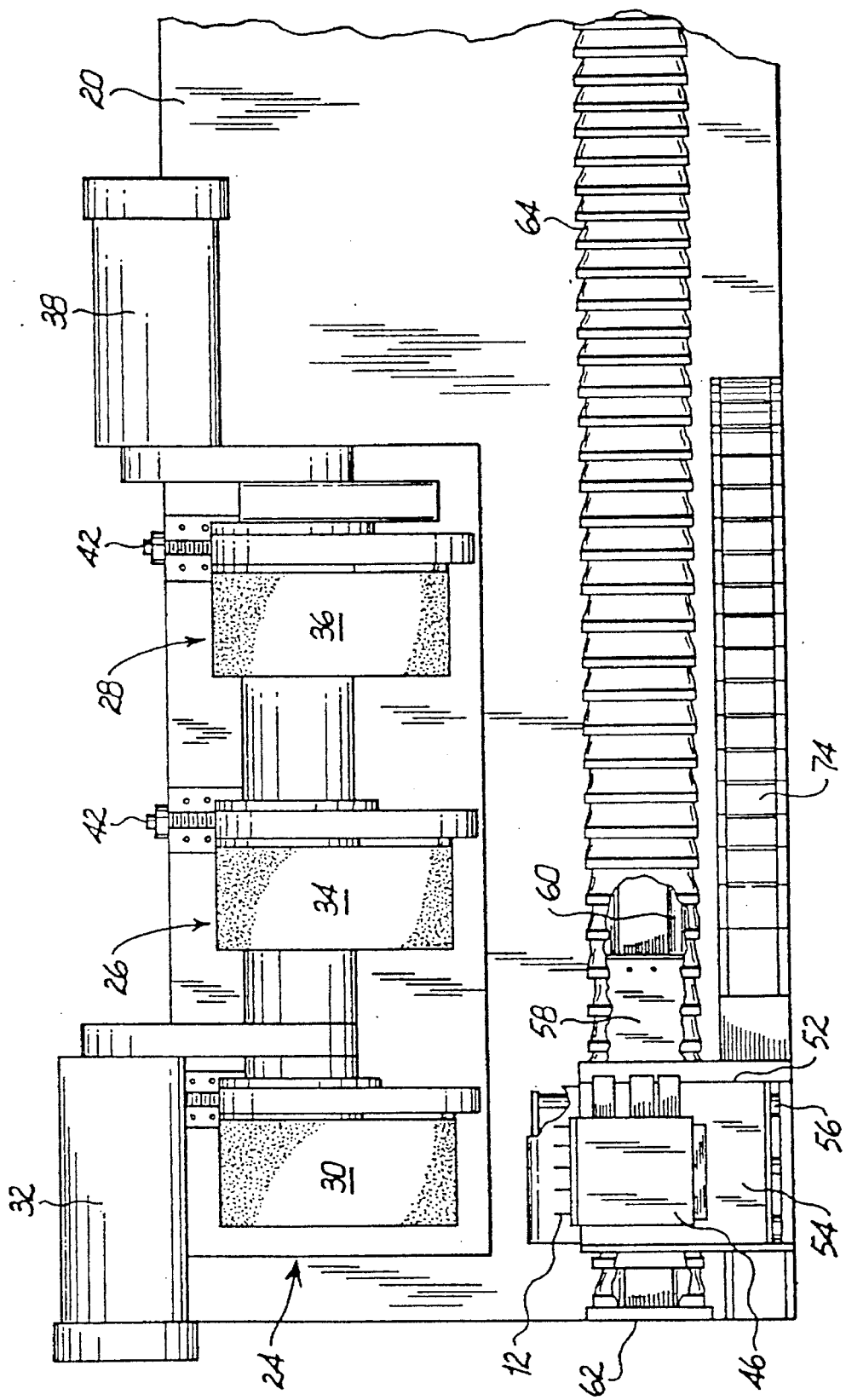
FIGS. 3–5 are top plan views illustrating a needle processing sequence using the apparatus of FIG. 1.
Figure 4:
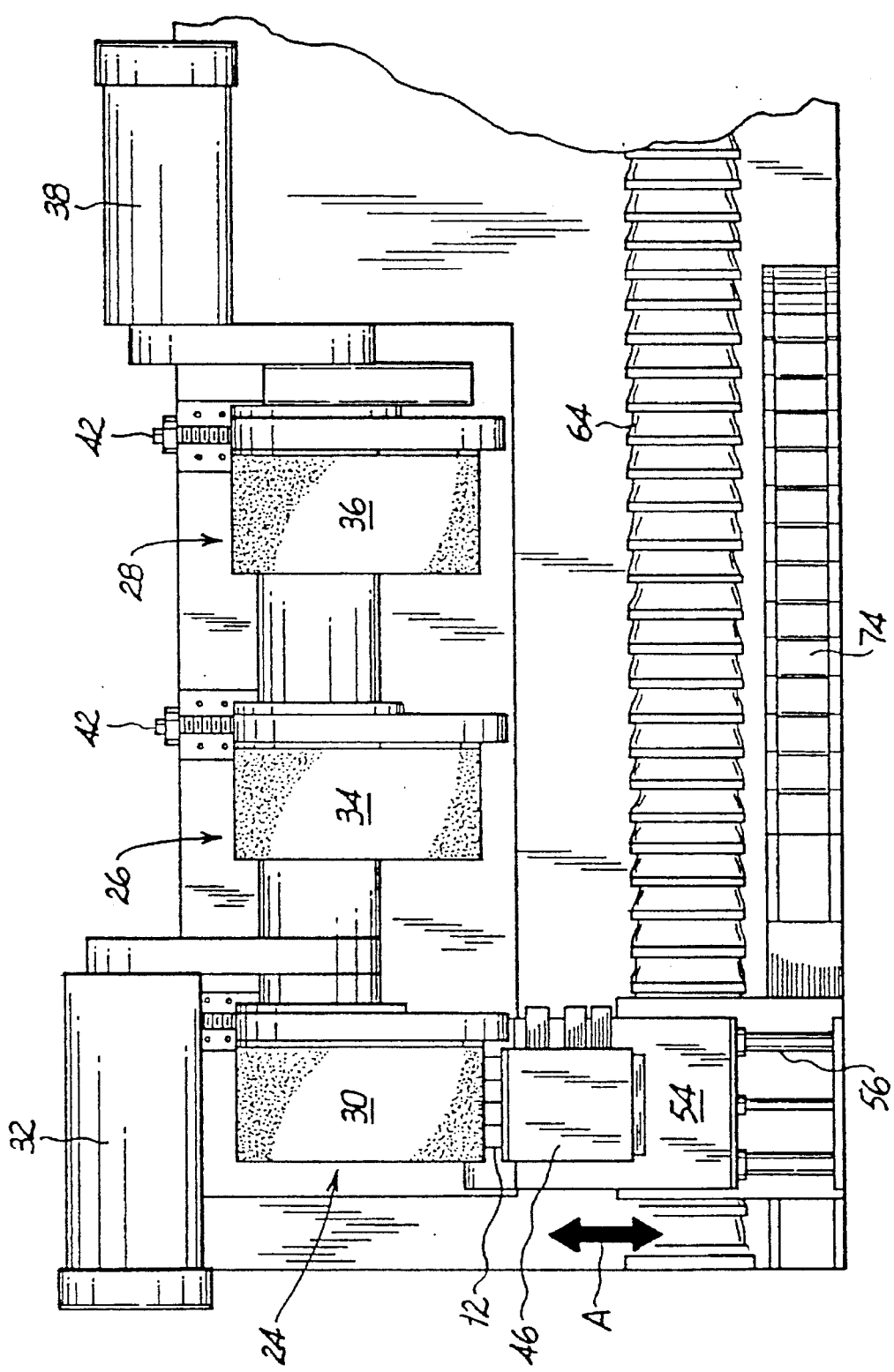
Figure 5:
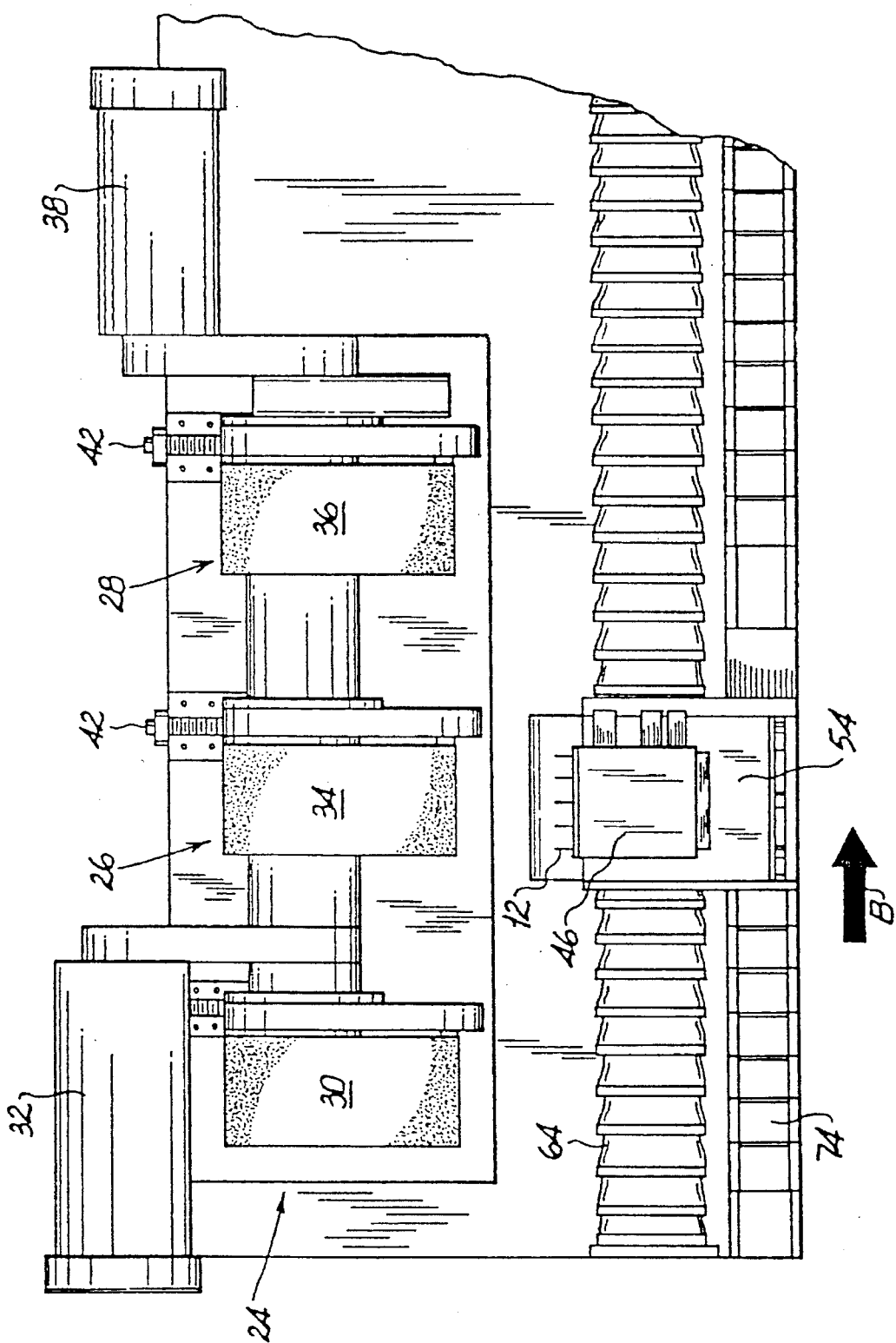

As seen in FIG. 1, the angle of the belts in relation to the needle blanks may be varied by adjusting the height of the abrading devices 24, 26 and 28 utilizing adjusting rods 40. In addition, as best seen in FIGS. 3–5, the distance between the belts and the rest position of the needle clamp 46 may be regulated by adjusting knobs 42 to advance or retract the belts. In an alternative embodiment the tension on the belts may be adjusted using mechanism 103 shown in FIG. 11.

The abrasive belt at each of the abrading devices 24, 26 and 28 each preferably have an abrasiveness having micron values of between about 0.3 microns to about 100 microns. While abrasive belts are preferred, it is also contemplated that abrasive wheels and grinding wheels may also be employed.

While the preferred embodiment utilizes three abrading devices, it is also contemplated that an alternative apparatus may include any number of abrading devices for fashioning a cutting edge on a needle blank instead of a series of processing stations. The envisioned alternative apparatus may include a variable speed motor for rotating an abrasive belt at different speeds. Further, a series of belts can be interchangeably fitted on a rotating structure to provide various abrasive surfaces.

Figure 2:
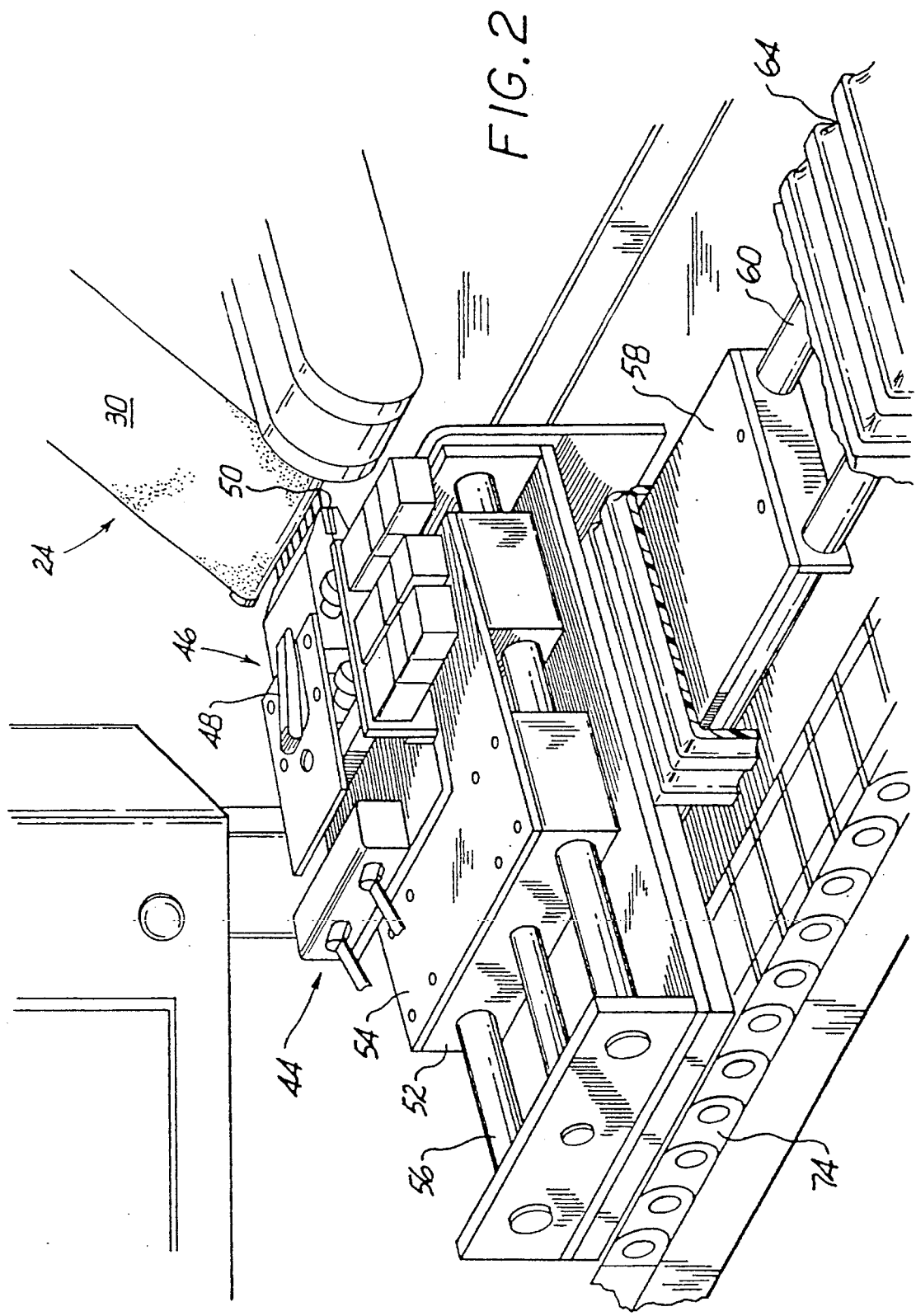
FIG. 2 is an enlarged perspective view illustrating the needle holding mechanism of the apparatus shown in FIG. 1.

Referring now to FIG. 2, a needle holding mechanism 44 is shown which includes a needle clamp 46 dimensioned and configured to hold at least one needle blank 12, or a multiplicity of needles 12 as shown. The needles 12 are releasably held in the clamp 46, which may be disengaged as seen in FIG. 6 to remove the needles 12 from the clamp 46. This is accomplished by moving lever 48 upwardly to open the jaws 50 of the needle clamp 46.

The needle holding mechanism 44 comprises an upper rod carriage 52 having a mounting block 54 for positioning the needle clamp 46 thereon. The mounting block 54 is slidably positioned on upper rods 56 connected to the upper rod carriage 52. The mounting block 54 slides along upper rods 56 in a substantially perpendicular direction from the abrading stations 22. Thus, the mounting block can be moved towards and away from the abrading devices 24, 26 and 28 in a smooth manner. The upper rod carriage 52 may also be moved parallel to the abrading stations 22 through the provision of a lower rod carriage 58. The lower rod carriage 58 and the upper rod carriage 52 are mounted to each other in overlapping relation. As the lower rod carriage 58 moves along an axis parallel to the abrading stations 22, it carries the upper rod carriage 52, as well as mounting block 54 and clamp 46.

The lower rod carriage 58 is slidably connected to a series of lower rods 60. The lower rods 60 are secured to plates 62 (see FIGS. 1 and 5) on the frame 18 and extend along an axis parallel to the abrading stations 22. Thus, as the lower rod carriage 58 moves along the lower rods 60, the lower rod carriage 58 moves parallel to the abrading devices 24, 26 and 28. The upper rod carriage 52, attached to the lower rod carriage 58, moves in concert with the lower rod carriage 58. The upper rod carriage 52 can thus be positioned adjacent to each of the belts of the abrading devices 24, 26 and 28.

At some point, due to the length of rods 60, there may be some downward deflection of rods 60 as the carriages 52, 58 move therealong. In such instances rather than rods, a linear way is substituted therefore. The linear way includes a track mounted directly to surface 20 to avoid the possibility of downward deflection. The lower carriage 58 rides in longitudinal channels formed in the track and is provided with guides on its underside which provide smooth movement of the carriage along the track.

The lower rod carriage 58 is protected from debris during the abrading process by a cover 64. Preferably, the cover 64 is flexible and has an accordion-like appearance. The cover 64 discourages debris such as metal shavings and the like discharged from the abrading stations 22 from collecting on the lower rods 60 and interfering with the movement of the lower rod carriage 58 along the lower rods 60. The cover 64 shrouds the full length of the lower rods 60 as seen in FIG. 1. As the rod carriages 52 and 58 are moved laterally, the cover 64 flexibly moves with the rod carriages 52 and 58 compressing and expanding appropriately. As best seen in FIGS. 3–5, mounting block 54 extends almost directly under the needles 12 to cover the front portion of the upper rod carriage 52. Mounting block 54 discourages debris from collecting on the front portion of the upper rod carriage 52 and interfering with carriage 52 during positioning along rods 56.

The needle clamp 46 is provided to hold one or a multiplicity of needles during engagement with the belt at each abrading station 22. A suitable needle clamp is that disclosed in copending U.S. application Ser. No. 07/959,151, filed Oct. 9, 1992, entitled NEEDLE TRANSPORTING APPARATUS, the disclosure of which is incorporated herein by reference. Hydraulic cylinders 66 are provided and are operably connected to the upper and lower rod carriages 52 and 58. Needles 12 are held in the needle clamp 46 and engage the belts at each abrading device 24, 26 and 28 in a controlled manner. Hydraulic cylinders 66 control the movement of upper and lower rod carriages 52 and 58 and the needle clamp 46 mounted thereon. Hydraulic cylinders 66 respond to instructions provided by an operator through operator interface 68 which sends electrical impulses to a programmable logic controller which activates hydraulic cylinders 66 via known mechanisms. Rod carriages 52 and 58 and the needle clamp 46, are thus capable of selective manipulation as will be described below.

Further, the hydraulic cylinders 66 enable the needles 12 held in needle clamp 46 to be moved toward and away from each belt at predetermined time intervals via upper rods 56. In addition, the speed at which the needles are moved toward each belt, i.e., the plunge speed, can be controlled as desired. Where coarser abrasive belts are used, a quick plunge speed may be desired to control the amount of material removed from the needle and to avoid excessive heat build up. When the needles are being plunged into a polishing belt, a relatively slower plunge rate may be utilized since for the removal of scratches a slower plunge speed is preferred. The controlled movement of the upper rod carriage 52 along the upper rods 56 enables the needles 12 to engage and disengage each belt for a short or long period of time, as well as, repetitive timed intervals if desired. Thus, the controlled and selectable movement of the rod carriages 52 and 58 provides predeterminable grinding and abrading to achieve a specified needle cutting edge.

It is further envisioned that other methods of moving the rod carriages 52 and 58 may be used other than hydraulic cylinder 66, such as, methods utilizing pneumatics, servomotors, and the like.

Further, the hydraulic cylinders 66 can be used to manipulate the needles 12 held in the needle clamp 46. Specifically, the needles 12 can be rotated while being held in the needle clamp 46. The needle clamp 46 includes a movable jaw 70 and a stationary jaw 72, as best seen in FIG. 6. Manipulation of the movable jaw 70 laterally with respect to the stationary jaw 72 rotates the needles 12 therebetween, to apply cutting edges 16 to various sides of needle 12.

The hoses leading to cylinders 66 are preferably positioned within a flexible articulated receptacle 74. The receptacle 74 is a linked housing which is positioned on the working surface 20 in an overlapped or folded manner and folds and unfolds as the needle holding mechanism 44 and clamp 46 are moved laterally along lower rods 60.

In operation, referring to FIGS. 3–5, the needles 12 held in the needle clamp 46 are positioned in an initial position substantially perpendicular to the first abrasive belt 30 of the first processing station 24, as shown in FIG. 3. The needle clamp 46 is placed on plate 55 and moved via upper carriage 52 on upper rods 56 in the direction of Arrow "A", as seen in FIG. 4, to a position tangential to the first belt 30 to engage the needles 12 with the first belt 30 for a selectable time interval or dwell period. In general, the needle clamp 46 preferably engages the needles 12 with belt 30 for about 100 millisecond to about 30 seconds.

The planar orientation of plate 55 can be adjusted by screw 59 thereby altering the attitude of the needles as they are presented to the belts. By turning screw 59 in one direction, plate 55 pivots upward about an axis defined by front edge 57 of plate 55 as the lower end of screw 59 contacts mounting block 54. Reversing the direction in which screw 59 is turned, plate 55 can be lowered. The planar orientation of plate 55 can preferably be adjusted in a range from 30° above the horizontal to 30° below the horizontal. It is also contemplated that the planar orientation of plate 55 can vary in a predetermined manner as the upper carriage 52 moves toward the belt whereby the needles engage the belt at various angles during the plunge into the belt.

Following grinding the needles 12 with the first belt 30, the needles 12 may be moved away from belt 30, rotated as described above, and then moved to re-contact belt 30. Rotating the needles 12 enables different portions of the needle 12 to be engaged with the belt 30.

After grinding the needles 12 at the first abrading device 24, the needles 12 held in needle clamp 46 are returned to their initial position by moving upper carriage 52 along rods 56 in the direction of Arrow "A" away from belt 30, back to the position shown in FIG. 3. The needles 12 are then moved laterally as seen in FIG. 5 in the direction of Arrow "B" with carriages 52 and 58 via the lower rods 60 to a position substantially perpendicular to the second belt 34 of the second abrading device 26. The needles 12 are then moved towards second belt 34 to be tangentially engaged with the second belt 34 in essentially the same manner as with the previous first abrading device 24 by moving carriage 52 along rods 56 towards belt 34, as indicated above with respect to FIG. 4.

The second belt 34 preferably has an abrasiveness less than that of the first belt 30. Second belt 34 engages the incomplete cutting edge 16 of the needles 12 to further refine the cutting edge. Further, the length and frequency of the time intervals of needle engagement with the second belt 34 may be adjusted in relation to those used with the first belt 30 for attaining optimum processing results. The needles 12 may also be rotated in a similar manner as described previously to further fashion a multi-sided cutting edge.

After grinding of the needles 12 at the second abrading device 26, the needles are returned to their position substantially perpendicular to the second belt 34 so that they can be moved to the third abrading device 28. The needles 12 held in the needle clamp 46 are then moved via the lower rods 60 in a manner similar to that described above, to a position substantially perpendicular to the third belt 36.

At the third abrading device 28, the needles 12 are tangentially engaged with belt 36 in a manner similar to that as disclosed in relation to the two previous abrading devices 24 and 26. However, the third belt 36 is preferably less abrasive than the first two belts 30 and 34 so that the cutting edge of the needles 12 can be deburred and polished. Preferably, belt 36 is a velvet flock belt which refines the cutting edge 16.

After the cutting edges 16 of the needles 12 have engaged the polishing belt 36, the needle clamp 46 is returned to its initial position opposite the first processing station 24, as shown in FIG. 3, via the upper and lower rod carriages 52 and 58.

Referring now to FIG. 6, the needle clamp 46 can then be removed from the mounting block 54. The needle clamp 46 is removably positioned on the mounting block 54, and a groove 76 in the stationary jaw 72 of the needle clamp 46 removably receives mounting bar 78 on mounting block 54.

After the cutting edges 16 of the needles 12 have been applied by apparatus 10, the needle clamp 46 is lifted off the mounting block 54, so that needles can then be removed from the needle clamp 46 by moving the lever 48 upwardly to release the jaws 50 of the clamp 46 which hold the needles 12.

It is envisioned that other means for holding a needle or plurality of needles may be used, such as, a fixed clamp device, or a slotted element for receiving needles.

It is further contemplated that the needle clamp 46 may be moved to desirable positions using other methods than the preferred embodiment described above. For example, slidable plates can be mounted on the lower rod carriage 58 and be used instead of the upper rod carriage 52. The slidable plates may be configured and dimensioned to receive the needle clamp 46 and slide in relation to one another such that the clamp can be moved towards and away from the processing stations.

It is evident from the above described preferred embodiment that various belt speeds and belt abrasiveness may be used, as well as various selectable timed intervals of needle engagement with the belts.

In addition to using abrasive belts, grinding wheels are a useful alternative, particularly where various grinding profiles are desired to be imparted to the needle blanks. The grinding wheel of the present invention is preferably fabricated from a preformed substrate to which an abrasive is bonded. In a particularly useful embodiment, the substrate is made from a metal or alloy, such as, for example, an aluminum-based material, and has an abrasive coating bonded to it by electroplating. The abrasives used for such bonding are diamond or cubic boron nitride ("CBN"), available under the tradename Borazon. Electroplated wheels may be manufactured to provide any custom design or according to any given specification and therefore, offer immediate fast cutting as purchased without the need for manual dressing of the grinding wheel prior to use. The cutting edges of super-abrasive materials do not break off as do those of conventional bonding materials. Instead, they wear down gradually over a long period of time. Therefore, grinding wheels plated with the above-mentioned abrasives provide the exact grinding surface geometry required for precision grinding. The variations inherent in the manual dressing or re-dressing to generate and retain the form of conventional bonded grinding wheels are not introduced into the needle forming process in the preferred embodiments of the present invention. In addition, in the preferred embodiments, no break-in period is required and wheel cores are reusable, thus reducing replacement costs.

Figure 12:
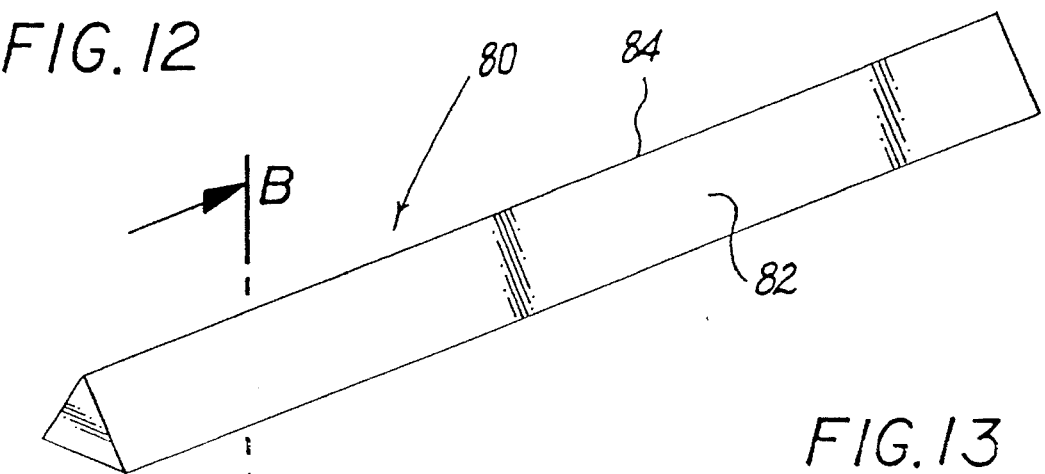
FIG. 12 is a side view of a needle blank with a triangular cross section.
Figure 13:
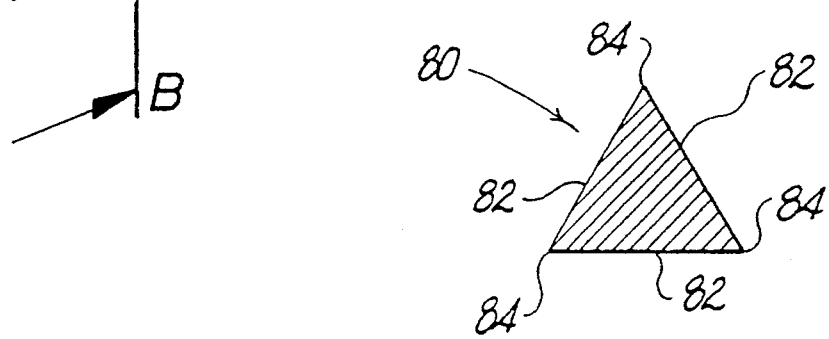
FIG. 13 is an end view taken along line B—B of FIG. 12.
Figure 14:
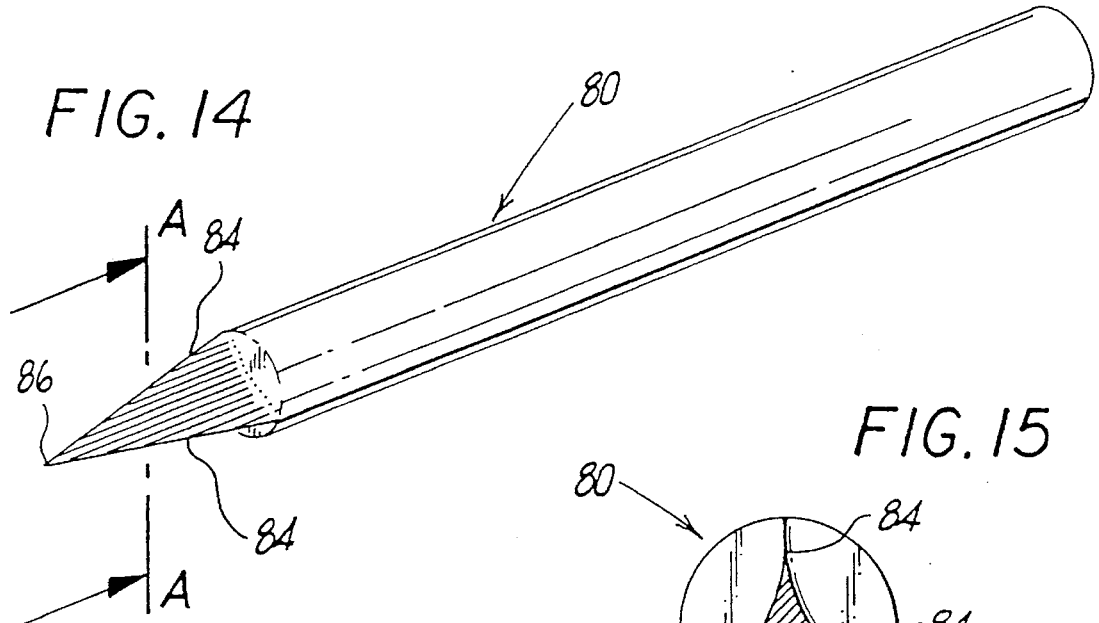
FIG. 14 is a side view of a partly circular partly triangular needle which has been hollow ground.
Figure 15:
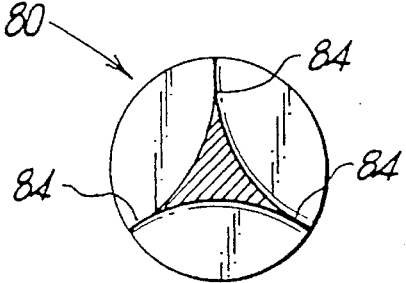
FIG. 15 is a sectional view taken along line A—A of FIG. 14 of the partly circular partly triangular hollow ground needle.

FIGS. 12 and 13 illustrate a portion of a needle blank 80 which has a triangular cross-sectional shape with three flat sides 82. The triangular cross-sectional shape may be imparted to the needle blank using any conventional means such as, for example, pressing or grinding. The term "needle blank" refers to the material from which the needle is formed, (i.e. the linear piece of metal which can be ground, pointed and polished, etc.) to form a finished needle and includes the intermediate material on which one or more processing steps has already been performed. Needle blank 80 may be fabricated from any alloy suitable for use in surgical needles such as stainless steel. The purpose of the grinding wheel of the present invention is to "hollow grind" the sides into a concave configuration as shown in FIGS. 14 and 15. One can readily see that edges 84 of the needle 80 in FIG. 15 can be ground and polished to a higher degree of sharpness than edges 84 of flat sided needle 80 of FIG. 13. An end of the needle blank may also be simultaneously tapered into a sharp point. FIGS. 14 and 15 illustrate a needle blank 80 which has been pressed, hollow ground to form sharp edges 84, and tapered to a sharp point 86.

Figure 16:
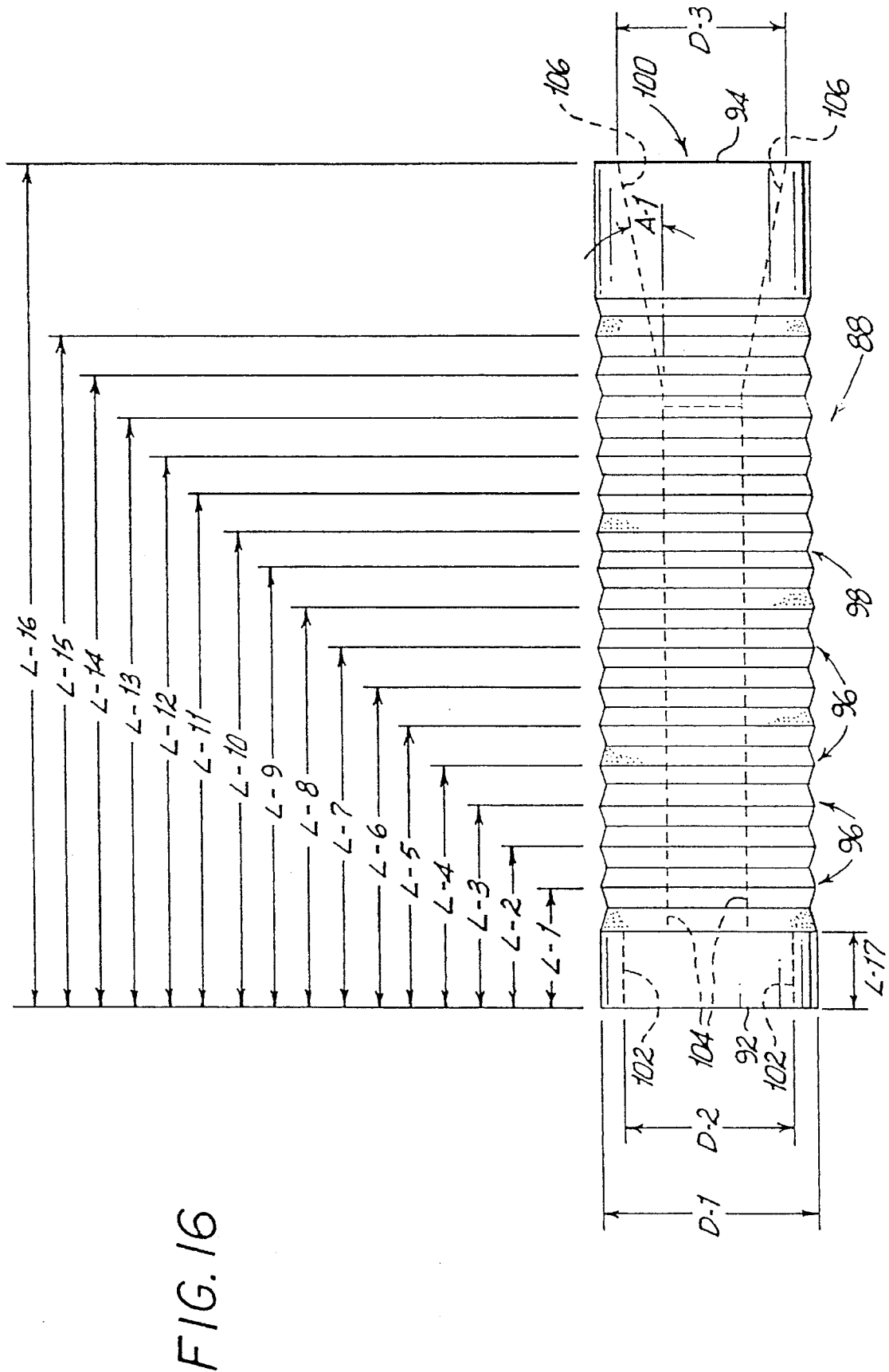
FIG. 16 is an elevational view of the grinding wheel of the present invention.
Figure 17:
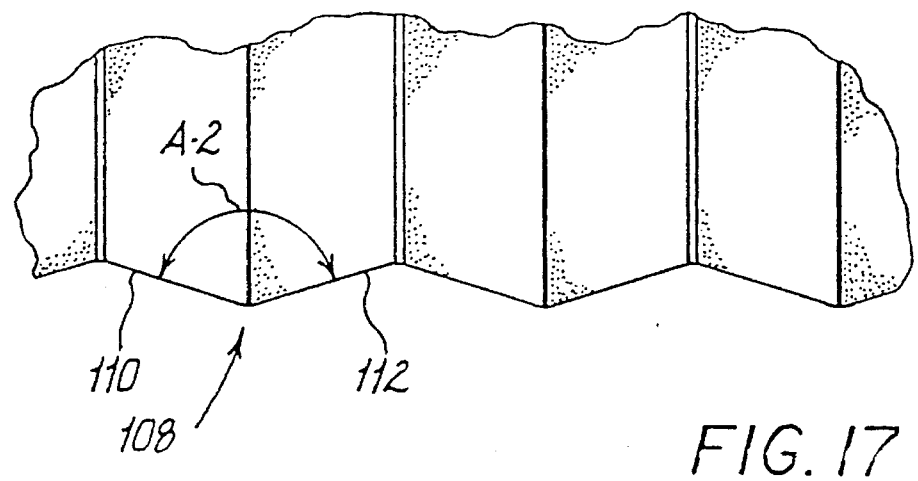
FIG. 17 is an enlarged plan view of the grinding edge of the grinding wheel.
Figure 18:
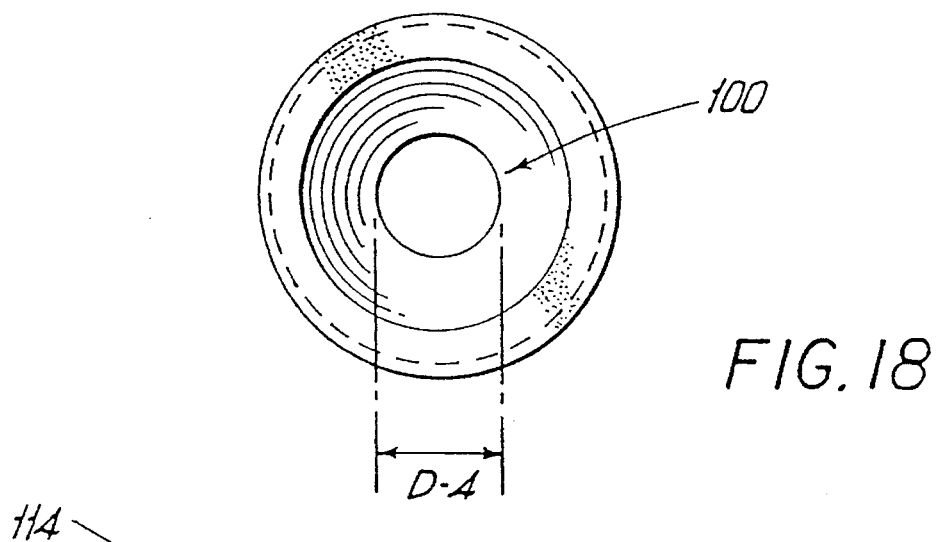
FIG. 18 is an end view of the grinding wheel.

The grinding wheel 88 of the present invention is illustrated in FIGS. 16, 17 and 18, to which are now referred. The dimensions given below should not be considered as limitations of the invention, but only as exemplifications of preferred embodiment(s) thereof. Any dimensions suitable for the purposes described herein may be employed with the appropriate tolerances. Grinding wheel 88 comprises a generally cylindrical shaft 90 having a first end portion 92, a second end portion 94, a plurality of circumferentially extending grinding ridges 96 extending circumferentially around middle portion 98, and an aperture or bore 100. The outer diameter D-1 of the wheel 88 is preferably from about 0.7500 inches to about 2.5000 inches and, in a more preferred embodiment, about 1.1250±0.001 inches. The length L-16 of grinding wheel 88 is preferably from about 2.0000 inches to about 6.0000 inches, and in a more preferred embodiment, is about 4.0000±0.0001 inches.

The longitudinally extending aperture 100 has first, second and third inner surface portions. A first inner surface portion 102 generally defines a cylinder having a diameter D-2 of from about 0.5000 to about 2.0000 inches. A second inner surface 104 defines a cylinder having a diameter D-4 of from about 0.2500 inches to about 1.0000 inches. A third inner surface 106 defines a generally frustoconical shape having a smaller diameter equal to the diameter D-4 of the second inner surface and a larger diameter D-3 of from about 0.5000 inches to about 1.5000 inches. The third inner surface is inclined from the axial or longitudinal center line by an angle A-1 of from about 5 degrees to about 15 degrees.

The length L-17 of the first end portion 92 can be from about 0.1000 inches to about 0.5000 inches.

The ridges 96 each are defined by an apex 108 formed at the conjunction of sides 110 and 112. The needle blanks are contacted to respective apexes to achieve the hollow grind of the needle. Angle A-2 formed by sides 110 and 112 can be from about 90 degrees to about 175 degrees. Preferably the angle formed by the sides of the ridges is between about 140 and 160 degrees and is most preferably about 150 degrees. In a preferred embodiment, the apexes are spaced apart from the first end by the respective distances L-1 to L-15 as set forth in Table A below. The apexes are spaced apart from each other a distance of 0.1875 inches, as can be seen from Table A. Tolerances should be ±0.0001 inches.

TABLE A

| Designation | Dimension (inches) |
| --- | --- |
| L-1 | 0.5875 |
| L-2 | 0.7750 |
| L-3 | 0.9625 |
| L-4 | 1.1500 |
| L-5 | 1.3375 |
| L-6 | 1.5250 |
| L-7 | 1.7125 |
| L-8 | 1.9000 |
| L-9 | 2.0875 |
| L-10 | 2.2750 |
| L-11 | 2.4625 |
| L-12 | 2.6500 |
| L-13 | 2.8375 |
| L-14 | 3.0250 |
| L-15 | 3.2125 |

The needle blanks 80 are preferably held in a support frame in side by side spaced apart relation, each needle being supported so as to contact a respective one of the apexes of the ridges 96 while the grinding wheel 88 is rotated around its longitudinal axis.

The grinding wheel 88 is preferably spun at from about 1,000 rpm to about 15,000 rpm to accomplish the grinding. Each side 82 of the needle blanks is, in turn, ground to produce the hollowed out (i.e. concave) shape oriented along the length of the needle blank as shown in FIG. 13. The end of the needle blank may simultaneously be tapered by grinding to a sharp point 86 as shown in FIG. 14.

Figure 19:
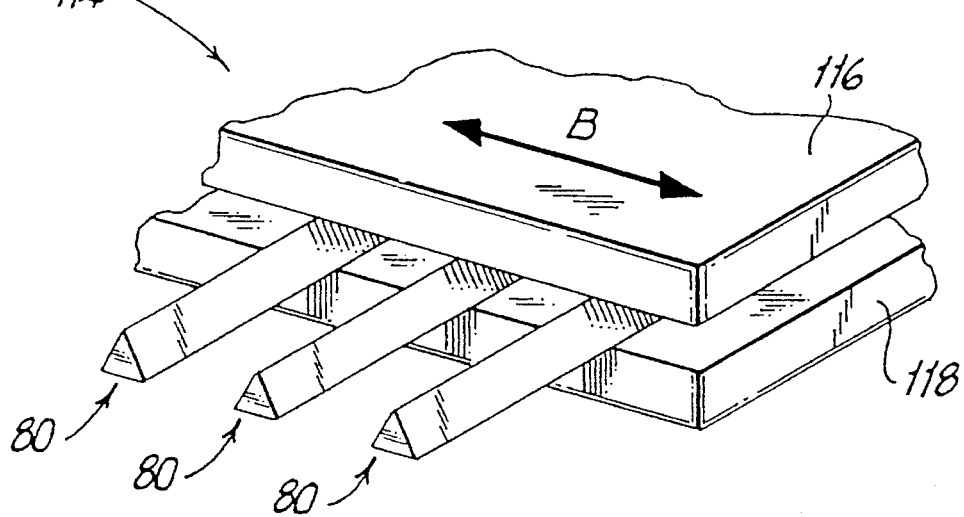
FIG. 19 is a perspective view of a fixture for holding a plurality of needle blanks for grinding.

FIG. 19 illustrates a fixture 114 for holding a plurality of needle blanks 80. The needle blanks 80 preferably have a triangular cross section.

The holding fixture 114 includes two flat parallel plates 116 and 118 between which needles 80 are frictionally held. Groves may be provide in one of the plates to ensure accurate placement of the needle blanks in relation to the ridges on the grinding wheel. The spacing of the needles within the jaws of the holder may correspond to the spacing of the ridges 96 on grinding wheel 88. The needle blanks may be placed within the plates of the holder and contacted with the grinding wheel. When grinding is complete on one flat side of the needle blank, the blanks may be manually rotated within the holder so that another flat face of the needle blank is positioned for contact with the grinding wheel. When grinding of the second face is complete, the process may be repeated to hollow grind the third face.

Preferably, one of plates 116 is laterally movable with respect to the other 118, as shown by arrows B. Lateral movement of plate 116 causes the needle blanks 80 to simultaneously rotate along their respective longitudinal axes, each thereby flipping over to another side. Thus, the needles 80 are placed in holder 114, which is thereafter positioned in a grinding apparatus for hollow grinding and tapering one side of the exposed ends of the needles 80. Then, plate 116 is laterally moved to turn the needles over and another side is ground and tapered. Finally, the needles are once again turned and the third side is ground and tapered.

Most preferably, the needle blanks are rotated on their longitudinal axis within the holder such that essentially no lateral movement of the needle blank occurs during rotation. When rotation directly on the axis of the needle blank is achieved, the holder need only be precisely oriented with respect to the grinding wheel once, since the position of the needle blank does not change as other faces of the needle blank are presented for grinding. A particularly useful holder for providing rotation of the needle blanks on their longitudinal axis with essentially no translational movement is described in U.S. application Ser. No. 07/959,151, filed Oct. 9, 1992, entitled NEEDLE TRANSPORTING APPARATUS, the disclosure of which is incorporated herein by reference.

The needles may optionally be polished on another wheel having a polishing surface configured and dimensioned similar to grinding wheel 88.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto. For example, while the invention has been described in terms of the preferred electroplated grinding wheels, it should be understood that other types of wheels having the disclosed geometry may be employed, such as, for example solid vitrified CBN wheels.

Referring to FIGS. 20–22 there is illustrated a second preferred embodiment of an apparatus 120 for applying a cutting edge to surgical needles. Apparatus 120 is particularly suited for use with hollow grinding wheel 88 of FIGS. 16 to 18. Apparatus 120 applies at least one cutting edge 84 on blank 80, and in a preferred embodiment, three edges 84 are applied as seen in FIGS. 13–15.

Referring to FIG. 20, the apparatus 120 includes a frame or table 122 having a working surface 124. The apparatus 120 comprises a series of abrading stations 126 positioned on work surface 124 for abrading a multiplicity of needles to apply cutting edges thereon. Abrading stations 126 refine needle blank 80 in sequential stages using rotating abrasive devices such as grinding belts or grinding stones and wheels. Each abrading device of station 126 preferably represents a predetermined stage of needle refinement.

As with apparatus 10 above, the present embodiment of apparatus 120 processes a needle blank 80 to result in three cutting edges 84 utilizing three separate abrading devices 128, 130 and 132. Alternative embodiments, however, may have more or less than three abrading devices, and further may provide cutting edges on more or less than three sides.

Apparatus 120 includes three rotatable abrading stations 126, preferably utilizing the above mentioned grinding wheels 88, positioned laterally adjacent to and along a common axis with each other. Abrading devices 128, 130 and 132 are rotated by motors 134, 136 and 138 by means of belts 135, 137 and 139 at predetermined speeds. Preferably grinding wheels 88 are similar to grinding wheel 88 described hereinabove having 150° ribs. Further, in the preferred embodiment, the first grinding station has a rough hollow grind wheel, the second station has a medium hollow grind wheel and the third station has a hollow grind polishing wheel.

A fourth station 140 may comprise a velvet flock belt 142 to provide for deburring and polishing. A motor 141 is provided to rotate belt 142. However, deburring may also be accomplished by reversing the direction of third wheel 88. Also, the speed of motor 138 may be adjusted for optimum polishing of the cutting edge.

Each of abrasive wheels 88 at abrading devices 128, 130 and 132 preferably have an abrasiveness having micron values of between about 0.3 microns to about 100 microns. While abrasive wheels are preferred, it is also contemplated that abrasive belts may also be employed.

As mentioned with respect to apparatus 10 above, it is also contemplated that an alternative apparatus may include any number of abrading devices for fashioning a cutting edge on a needle blank instead of a series of processing stations. The envisioned alternative apparatus may include a variable speed motor for rotating an abrasive wheel at different speeds.

Referring now to FIGS. 21 and 22, a needle holding mechanism 144 is shown which includes a needle clamp 146 dimensioned and configured to hold at least one needle blank 80, or a multiplicity of needles 80 as shown in FIG. 20. Needles 80 are releasably held in clamp 146, which may be disengaged to remove needles 80 from clamp 146. This is accomplished by moving lever 148 upwardly to open jaws 150 of needle clamp 146.

Needle holding mechanism 144 comprises an upper rod carriage 152 having a mounting block 154 for positioning needle clamp 146 thereon. Preferably clamp 146 is detachably mounted on a plate 153 affixed to mounting block 154. Mounting block 154 is slidably positioned on upper rods, similar to rods 56 in apparatus 10 above, connected to upper rod carriage 152. Mounting block 154 slides along upper rods in a direction substantially perpendicular to the abrading stations 126. Thus, mounting block 154 can be moved towards and away from abrading devices 128, 130 and 132 in a smooth manner.

Immediately below upper rod carriage 152, and slidably mounted thereto, is a vertical plunge plate 156 which is mounted upon and moves along an angled track 158. Vertical plunge plate is provided to alter the height of needle clamp 146 during the grinding sequence thereby providing an additional axis of motion in a vertical direction. By moving vertical plunge plate 156 along track 158 upper rod carriage 152, and thus needle clamp 146, may be moved upwardly and inwardly or rearwardly and downwardly. Preferably, angled track 158 is oriented at an angle of from 5 degrees to 30 degrees with respect to work surface 124 and move preferably at an angle of 9 degrees.

Upper rod carriage 152 and vertical plunge plate 156 may also be moved parallel to abrading stations 126 through the provision of a lower rod carriage 160. Lower rod carriage 160 and track 158 are mounted to each other in overlapping relation. As lower rod carriage 160 moves along an axis parallel to abrading stations 126, as shown in FIG. 20, it carries vertical plunge plate 156 and upper rod carriage 152, as well as mounting block 154 and clamp 146.

As with apparatus 10 above, lower rod carriage 160 is slidably connected to a series of lower rods 161 extending along an axis parallel to abrading stations 126. Thus, as lower rod carriage 160 moves along lower rods 161, lower rod carriage 160 moves needle holding mechanism parallel 144, of which lower rod carriage 160 is a part, to abrading devices 128, 130 and 132. Thus upper rod carriage 152 can be positioned adjacent to each of wheels 88 of abrading devices 128, 130 and 132.

As above, a linear way may be substituted for the rods. The linear way includes a track mounted directly to surface 124 to avoid the possibility of downward deflection. Lower carriage 160 rides in longitudinal channels formed in the track and is provided with guides on its underside which provide smooth movement of the carriage along the track.

Lower rod carriage 160 and vertical plunge plate 156 are also protected from debris during the abrading process by a flexible cover 162. As needle holding mechanism 144 is moved laterally, cover 162 flexibly moves with upper rod carriage 52 and vertical plunge plate 156 compressing and expanding appropriately to prevent accumulation of debris.

As above, a suitable needle clamp for use with the present embodiment is that disclosed in copending U.S. application Ser. No. 07/959,151, filed Oct. 9, 1992 entitled NEEDLE TRANSPORTING APPARATUS, the disclosure of which is incorporated herein by reference.

Hydraulic cylinders 164 are provided and are operably connected to upper and lower rod carriages 152 and 160, respectively, and vertical plunge plate 156 by means of hoses 165. Hydraulic cylinders 164 respond to instructions provided by an operator through operator interface, similar to interface 68 with respect to apparatus 10 hereinabove, which sends electrical impulses to a programmable logic controller which activates hydraulic cylinders 164 via known mechanisms. A computer numerical controller (CNC) is used to control motions, such as, for example X (station to station), Y(in and out feed), z(vertical) and U(rotation of needles in clamp) thus providing 4 axes of motion to needles 80. Preferably the movements are in increments of one ten thousandth of an inch. Rod carriages 152 and 160, vertical plunge plate 156 and needle clamp 146, are thus capable of selective manipulation as will be described herein below.

Further, hydraulic cylinders 164 enable needles 80 held in needle clamp 146 to be moved toward and away from each wheel 88 at predetermined time intervals via the upper rods. In addition, the speed at which needles 80 are moved toward each wheel 88, i.e., the plunge speed, can be controlled as desired. In addition to the speed of the plunge, the vertical height of needles 80, relative to grinding wheels 88, may be altered during the plunge by moving vertical plunge plate 156 along track 158 during the grinding sequence. This is particularly useful where it is desired to alter the depth of the grinding groove in a face of needle 80 to provide a tapered or elliptical groove.

For example, as needle 80 is plunged into grinding wheel 88, wheel 88 may cut deep and close to the needle axis, by moving vertical plunge plate 156 rearwardly, in the direction of arrow B in FIG. 22, and thus downwardly along track 158, the depth of the grind in a facing surface of needle 80 may be reduced as needle blank 80 is advanced into grinding wheel 88. Since vertical plunge plate 156 also moves rearwardly during this sequence, the inward movement of upper rod carriage 152 must be increased in an amount sufficient to offset the rearward movement of vertical plunge plate 156 in order to maintain a consistent inward plunge speed and thus allow a downward vertical move along with the inward plunge.

The controlled movement of upper rod carriage 152 along the upper rods, along with vertical plunge plate 156, enables needles 80 to engage and disengage each wheel 88 for a short or long period of time, as well as, repetitive timed intervals and depth of cuts if desired. Thus, the controlled and selectable movement of rod carriages 152 and 160 and vertical plunge plate 156 provides a variable and predeterminable grinding and abrading sequence to achieve a specified needle cutting edge profile.

As above, it is further envisioned that other methods of moving rod carriages 152 and 160 and vertical plunge plate 156 may be used other than hydraulic cylinder 164, such as, methods utilizing pneumatics, servo-motors, and the like.

Jaws 150 may be comprised of movable upper plate 116 and stationary lower plate 118 described hereinabove. Manipulation of movable plate 116 laterally with respect to stationary plate 118 rotates needles 80 therebetween to present successive sides 82 of needles 80 to wheel 88 in order to apply cutting edges 84 to various sides 82 of needle 80.

In operation, referring to FIGS. 20–22, needles 80 held in the needle clamp 146 are positioned in an initial position substantially perpendicular to, and slightly below, first abrasive wheel 88 of the first processing station 126, as shown in FIG. 21. Needle clamp 146 is placed on plate 153 and moved via upper rod carriage 152 on upper rods in the direction of Arrow "A", as seen in FIG. 22, to a position tangential to first wheel 88 to engage needles 80 with first wheel 88 which rotates in the direction of arrow "R" for a selectable time interval or dwell period. Additional inward and upward positioning may be obtained by initially moving vertical plunge plate 156 inward in the direction of arrow C in FIG. 21. In general, needle clamp 146 preferably engages needles 80 with wheel 88 for about 1.0 millisecond to about 5.0 seconds.

The planar orientation of plate 153 can be adjusted by screw 166 thereby altering the attitude of needles 80 as they are presented to wheels 88. The vertical orientation of plate 156 can be varied in a predetermined manner by means of vertical plunge plate 156, and thus needle clamp 146 and needles 80, as upper rod carriage 152 moves toward wheel 88 whereby needles 80 engage wheel 88 at various heights during the plunge into wheel 88.

Following grinding needles 80 with first wheel 88, needles 80 may be moved away from wheel 88, rotated between plates 116 and 118 as described hereinabove, and then moved to re-contact wheel 88. Rotating needles 80 enables different sides 82 of needle 80 to be engaged with the wheel 88.

After grinding needles 80 at first abrading device 128, needles 80 held in needle clamp 146 are returned to their initial position by moving upper rod carriage 152 along the rods away from wheel 88. Needles 80 are then moved laterally to a position substantially perpendicular to second wheel 88 of second abrading device 130. Needles 80 are then moved towards second wheel 88 to be tangentially engaged with second wheel 88 in essentially the same manner as with the previous first abrading device 128 by moving upper rod carriage 152 along the rods 56 towards wheel 88.

Second wheel 88 preferably has an abrasiveness less than that of first wheel 88. Second wheel 88 engages the incomplete cutting edge 84 of needles 80 to further refine the cutting edge.

After grinding of needles 80 at the second abrading device 130, needles 80 are returned to their position substantially perpendicular to second wheel 88 so that they can be moved to third abrading device 132. Needles 80 held in needle clamp 146 are then moved via lower rods 161 in a manner similar to that described above, to a position substantially perpendicular to third wheel 88.

At third abrading device 132, needles 80 are tangentially engaged with wheel 88 in a manner similar to that as disclosed in relation to the two previous abrading devices 128 and 130. However, third wheel 88 is preferably less abrasive than the first two wheels 88 so that the cutting edge of needles 80 can be deburred and polished.

Finally, after grinding of needles 80 at third abrading device 132, needles 80 are returned to their position substantially perpendicular to third wheel 88 so that they can be moved to a deburring and polishing belt 142. Belt 142 is a velvet flock belt which refines cutting edge 84.

After cutting edges 84 of needles 80 have engaged polishing belt 142, needle clamp 146 is returned to its initial position opposite the first processing station 128, similar to that of apparatus 10 as shown in FIG. 3, via upper and lower rod carriages 152 and 160.

After cutting edges 84 of needles 80 have been applied by apparatus 120, needle clamp 146 is lifted off mounting block 154, so that needles 80 can then be removed from needle clamp 146 by moving lever 148 upwardly to release jaws 150 of clamp 146 which hold needles 80.

It is envisioned that other means for holding a needle or plurality of needles may be used, such as, a fixed clamp device, or a slotted element for receiving needles.

Additionally, a simple block type clamp may be provided to hold a dressing tool for dressing the grinding wheels back to the proper angle. Preferably a diamond tool may be provided to fix all the grooves at once (a plunge dresser) or to fix a single groove (a single point dresser).

It is further contemplated that needle clamp 146 may be moved to desirable positions using other methods described herein above.

It is evident from the above described preferred embodiment that various wheel speeds and wheel abrasiveness may be used, as well as various selectable timed intervals of needle engagement with the wheels.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. An apparatus for applying a cutting edge to a needle blank comprising:
   a means for abrading at least one needle;
   b means for holding the needle; and
   c means for positioning said holding means in relation to said abrading means to selectively engage and disengage the needle with said abrading means, said positioning means including;
   i) means for moving said holding means in at least two directions while the needle is in contact with said abrading means wherein, one of said at least two directions is a vertical direction.

2. The apparatus according to claim 1, wherein said positioning means includes means for moving the needle along three axes.

3. The apparatus according to claim 1, wherein said positioning means includes means for altering the depth of the abrasion relative to a longitudinal axis of the at least one needle.

4. The apparatus according to claim 3, wherein said depth altering means includes a movable plate oriented at an angle relative to the longitudinal axis of the at least one needle such that the position of the longitudinal axis of the at least one needle relative to said abrading means is alterable as the needle is moved into and out of engagement with said abrading means.

5. The apparatus according to claim 4, wherein said plate is oriented at an angle of approximately 5 degrees to 30 degrees relative to said longitudinal axis of the at least one needle.

6. The apparatus according to claim 4, wherein said plate is oriented at an angle of approximately 5 degrees to 15 degrees relative to said longitudinal axis of the at least one needle.

7. The apparatus according to claim 1, further comprising means for moving said holding means parallel to a longitudinal axis of said abrading means.

8. The apparatus according to claim 1, wherein said positioning means includes means for varying the angle at which said abrading means contacts the needles.

9. The apparatus according to claim 1, further comprising means for rotating said abrading means.

10. The apparatus according to claim 9, wherein said abrading means comprises at least one grinding wheel.

11. The apparatus according to claim 7, further comprising means for deburring and polishing the needle, said positioning means moving said holding means from said abrading means to selectively engage and disengage the needle with said deburring means.

12. The apparatus according to claim 11, wherein said abrading means and said means for deburring and polishing are positioned in a common plane.

13. The apparatus according to claim 1, wherein said holding means comprises a clamp means having a pair of jaw members for releasably holding the needle therebetween, a first jaw member being movable in at least two planes in relation to a second jaw member.

14. The apparatus according to claim 13, further comprising means for rotating the needle within said clamp means to provide for contact of the needle with said abrading means on various sides of the needle, said rolling means moving said first jaw member in a plane parallel to said second jaw member.

15. The apparatus according to claim 13, wherein said clamp means is adapted for holding a plurality of needles.

16. The apparatus according to claim 10, wherein said abrading means further comprises a plurality of said grinding wheels, each wheel of said plurality of said grinding wheels having a different abrasiveness.

17. The apparatus according to claim 2, wherein said moving means moves the needle along an axis perpendicular to a longitudinal axis of said abrading device and parallel to a longitudinal axis of the needle.

18. The apparatus according to claim 2, wherein said moving means moves the needle along an axis perpendicular to a longitudinal axis of said abrading device and perpendicular to a longitudinal axis of the needle.

19. The apparatus according to claim 2, wherein said moving means moves the needle along an axis parallel to a longitudinal axis of said abrading means.

20. Apparatus according to claim 2, wherein said holding means further includes means for rotating the needle about a longitudinal axis of the needle.

21. The apparatus according to claim 2, wherein said abrading device comprises a plurality of rotatable abrasive wheels having differing abrasiveness.

* * * * *